United States Patent [19]

Jinbo et al.

[11] 4,340,768
[45] Jul. 20, 1982

[54] PROCESS FOR PRODUCING 4,4'-DIHYDROXYBIPHENYL

[75] Inventors: Susumu Jinbo; Shoichi Kohno; Masatoshi Onishi, all of Tokyo, Japan

[73] Assignee: Hodogaya Chemical Co., Ltd., Tokyo, Japan

[21] Appl. No.: 196,756

[22] Filed: Oct. 14, 1980

Related U.S. Application Data

[63] Continuation of Ser. No. 45,652, Jun. 5, 1979, abandoned.

[30] Foreign Application Priority Data

Jul. 18, 1978 [JP] Japan .................................. 53-86707

[51] Int. Cl.$^3$ ...................... C07C 37/02; C07C 37/72; C07C 37/84
[52] U.S. Cl. .................................... 568/730; 568/750
[58] Field of Search ............... 568/730, 748, 749, 750, 568/751, 752, 753

[56] References Cited

U.S. PATENT DOCUMENTS

| | | | |
|---|---|---|---|
| 2,675,412 | 4/1954 | Herbert et al. | 568/749 |
| 2,948,758 | 8/1960 | Filar | 568/754 |
| 3,155,734 | 11/1964 | Merkel | 568/749 |
| 3,413,341 | 11/1968 | Bursack et al. | 568/730 |
| 3,894,095 | 7/1975 | Pietzsch et al. | 568/749 |
| 4,113,974 | 9/1978 | Mark et al. | 568/750 |

*Primary Examiner*—Natalie Trousof
*Assistant Examiner*—L. Hendriksen
*Attorney, Agent, or Firm*—Oblon, Fisher, Spivak, McClelland & Maier

[57] ABSTRACT

4,4'-Dihydroxybiphenyl is produced by hydrolyzing 4,4'-dibromobiphenyl in the presence of a copper compound catalyst in an alkaline aqueous solution; extracting by-products from the alkaline aqueous solution with an alcohol or ketone which forms an organic phase; neutralizing or acidifying the alkaline aqueous solution with an acid; extracting the reaction product with the specific solvent; and crystallizing the reaction product from the extracted solution to obtain 4,4'-dihydroxybiphenyl having high purity.

9 Claims, No Drawings

PROCESS FOR PRODUCING 4,4'-DIHYDROXYBIPHENYL

This is a continuation, of application Ser. No. 045,652, now abandoned, filed June 5, 1979.

BACKGROUND OF THE INVENTION

1. Field of the Invention

The present invention relates to a process for producing a 4,4'-dihydroxybiphenyl having high purity by a special purification system after hydrolyzing 4,4'-dibromobiphenyl.

2. Description of the Prior Arts 4,4'-Dihydroxybiphenyl is useful as an antioxidant of a resin; an intermediate of a dye; and a starting material for polyesters, polyepoxides, polyurethanes and polycarbonates. This compound has been considered as a starting material for heat resistant resins. Accordingly, it has been required to supply 4,4'-dihydroxybiphenyl having a purity of greater than 98% and a content of inorganic salts of less than 30 ppm. This is relatively severe requirement. Since 4,4'-dihydroxybiphenyl has high melting point and low solubility etc., it is quite difficult to obtain 4,4'-dihydroxybiphenyl having the required quality.

In the conventional process for producing 4,4'-dihydroxybiphenyl, 4,4'-biphenyl disulfonic acid is molten with alkali metal hydroxide and then, hydrazine is added to the alkaline aqueous solution of the reaction product and then, it is neutralized to obtain a colorless 4,4'-dihydroxybiphenyl (Japanese Unexamined Patent Publication No. 68154/1977). However, this conventional process has an industrial difficulty on a wasted water treatment in the sulfonation.

The inventors have studied on a process for producing 4,4'-dihydroxybiphenyl by a hydrolysis of 4,4'-dihalobiphenyl. (Japanese Unexamined Patent Publication No. 22347/1979). In this process, a copper compound is used as a catalyst for hydrolyzing 4,4'-dibromobiphenyl in an alkaline aqueous solution, whereby 5–15% of by-products such as phenylphenols formed by dehalogenation and alkali soluble macromolecular compounds, are caused by the side reaction. When 4,4'-dihydroxybiphenyl is obtained by neutralizing the alkaline reaction mixture, these by-products are included in the product as the impurities. It has been difficult to obtain 4,4'-dihyroxybiphenyl having high purity. Moreover, crystals of 4,4'-dihyroxybiphenyl precipitated by neutralizing the alkaline reaction mixture are fine. The filtration is not easily performed and the inorganic salts such as sodium halides, are not easily removed from the filtered cake of the product obtained by the filtration, even though filtered cake is washed with water. It is impossible to purify 4,4'-dihydroxybiphenyl by a distillation so as to give the quality required for the demands in view of the characteristics of 4,4'-dihydroxybiphenyl.

SUMMARY OF THE INVENTION

It is an object of the present invention to provide a process for producing 4,4'-dihydroxybiphenyl having high purity by a hydrolysis of 4,4'-dihalobiphenyl.

It is another object of the present invention to provide a process for producing 4,4'-dihydroxybiphenyl having high purity by separating from the product formed from 2,4'-dihalobiphenyl.

The other object of the present invention is to provide a process for producing 4,4'-dihydroxybiphenyl having high purity by selectively extracting a by-product of sodium o- and p-phenylphenolate and then separating 4,4'-dihydroxybiphenyl from the other impurities such as macromolecular material.

The foregoing and other objects of the present invention have been attained by providing a process for producing 4,4'-dihydroxybiphenyl having high purity by hydrolyzing 4,4'-dibromobiphenyl in the presence of a copper compound catalyst in an alkaline aqueous solution; extracting by-products from the alkaline aqueous solution with an alcohol or ketone which forms an organic phase; neutralizing or acidifying the alkaline aqueous solution with an acid; extracting the reaction product with the specific solvent; and crystallizing 4,4'-dihydroxybiphenyl from the solvent solution.

DETAILED DESCRIPTION OF THE PREFERRED EMBODIMENTS

In accordance with the process of the present invention, 4,4'-dihydroxybiphenyl having high purity can be also obtained by using a crude 4,4'-dibromobiphenyl which contains 4-bromobiphenyl, 2-bromobiphenyl and 2,4'-dibromobiphenyl.

The specific solvents used in the present invention can be alcohols or ketones which form water immiscible phase.

Suitable alcohols include 1-butanol, 2-butanol, isobutanol, 1-pentanol, 2-pentanol, 1-hexanol, 1-heptanol, 2-heptanol, 1-octanol, 2-ethyl-1-hexanol and cyclohexanol, etc.

Suitable ketones include 2-hexanone, methyl isobutyl ketone, 2-heptanone, 4-heptanone, diisobutyl ketone, phorone, isophorone, cyclohexanone, acetophenone and methyl cyclohexanone. It is possible to use a mixture thereof.

It is also possible to use a mixture of the specific alcohol and the specific ketone or a mixture of one of the specific alcohol or ketone and an aromatic hydrocarbon such as toluene, xylene and monochlorobenzene or an aliphatic hydrocarbon such as n-hexane and ligroin. It is preferable to use only one kind of the specific alcohol or the specific ketone in view of recovery of the solvent.

When the specific solvent is used, only alkali metal o-phenylphenolates and p-phenylphenolates can be selectively extracted from an alkaline aqueous solution of the reaction product. When the alkaline aqueous solution is neutralized with an acid especially a mineral acid to form the reaction product in free form and the reaction product is extracted with the same specific solvent, the extract is easily separated from the water phase whereby inorganic salts are completely removed by a water washing.

Then, 4,4'-dihydroxybiphenyl is precipitated from the extract. The object compound is precipitated from the solvent by a concentration to remove the solvent, a dilution by admixing with a solvent which does not substantially dissolve 4,4'-dihydroxybiphenyl; or a cooling to reduce a solubility of 4,4'-dihydroxybiphenyl.

When the crude 4,4'-dibromobiphenyl is used, 2,4'-dihydroxybiphenyl and macromolecular compounds produced are remained in the extracted solution by the crystallization.

It is preferable to obtain the crystals by concentrating the extracted solution at usually 60 to 90% preferably 75 to 85% (based on the solvent) and then, admixing with a solvent which does not substantially dissolve 4,4'-dihydroxybiphenyl.

The temperature for extracting the alkaline aqueous solution of the reaction product with the specific alcohol or ketone is depending upon the kind of the specific solvent and it is usually in a range from 30° to 95° C. preferably from 50° to 85° C.

The amount of the solvent is decided by experiments in view of the apparatus and the other conditions. It is preferable to use the specific solvent for several times by dividing it.

The alkaline aqueous solution is neutralizing with a mineral acid such as hydrochloric acid, hydrobromic acid and sulfuric acid. The reaction product in free form is extracted with the specific solvent.

The temperature for the neutralization and the extraction is usually in a range of from 30° C. to 90° C. preferably from 70° C. to 85° C.

When the specific extracting solvent is the specific alcohol, it is possible to obtain a colorless 4,4'-dihydroxybiphenyl by a conventional reducing process in the alkaline aqueous solution of the reaction product or the solvent solution extracting the reaction product in free form.

The resulting 4,4'-dihydroxybiphenyl has a purity of greater than 98%, a content of p-phenylphenol of less than 1%, a content of macromolecular compound of less than 1%, a content of inorganic salts of less than 30 ppm. This has satisfactory quality as a commercial product required in market.

The important feature of the present invention is as follows. 4,4'-Dibromobiphenyl is converted into 4,4'-dihydroxybiphenyl with a copper catalyst such as a cuprous oxide in an aqueous solution of sodium hydroxide in an autoclave at an elevated temperature under an elevated pressure. The catalyst is separated by a filtration. The alkaline aqueous solution of the reaction product is extracted with 1-heptanol, 1-butanol, 1-octanol, 2-ethyl hexanol, 1-hexanol, cyclohexanol, cyclohexanone, 2-hexanone or 4-heptanone. The alkaline aqueous solution of the reaction product is neutralized with a mineral acid if desired in the presence of the specific solvent which is newly added. In the second extraction after the neutralization, it is preferable to use substantially the same specific solvent. The extracted solution is separated from the water layer and washed with water, concentrated under a reduced pressure to distill off most of the specific solvent such as 80%. The bottom residue is cooled and filtered and washed with a hydrocarbon and dried to obtain crystals of 4,4'-dihydroxybiphenyl.

It is preferable to perform a reduction before the crystallization. It is also preferable to treat with an active carbon before the crystallization.

In the other feature of the present invention, it is important to separate the by-product of 2,4'-dihydroxybiphenyl from the object product of 4,4'-dihydroxybiphenyl by crystallizing the object product from the extracted solution. The crystallization should be carried out under such conditions that the by-product 2,4'-dihydroxybiphenyl remains in the mother liquor. The condition can be easily determined by a simple test.

The present invention will be further illustrated by certain examples and references which are provided for purposes of illustration only and are not intended to be limiting the present invention.

EXAMPLE 1

In a reactor, 154 wt. parts of biphenyl was converted with a vapor of 384 wt. parts of bromine at room temperature for about 8 hours. The resulting reaction product was recrystallized from 1500 wt. parts of benzene to obtain 235 wt. parts of 4,4'-dibromobiphenyl. It was confirmed that the product was 4,4'-dibromobiphenyl by a gas chromatography and IR spectrum and a melting point of 165°–166° C.

In a 0.3 liter autoclave, 46.8 wt. parts of 4,4'-dibromobiphenyl, 200 wt. parts of 15% NaOH aqueous solution and 0.8 wt. part of cuprous oxide were charged. The autoclave was closed and purged with nitrogen and was heated. The reaction was carried out at 250° C. for 3 hours. The reaction mixture was filtered at 40°–50° C. to separate the catalyst of the cuprous oxide. The catalyst layer was washed with water. The washing water was mixed with the filtrate. The alkaline aqueous solution was heated at 80°–85° C. and was extracted for 3 times with 84 wt. parts of 1-heptanol. Then, 450 wt. parts of new 1-heptanol was added to the alkaline aqueous solution. The mixture was stirred at 80°–85° C. and neutralized with conc. hydrochloric acid. The reaction product in free form was immediately extracted into the 1-heptanol. The 1-heptanol layer was separated from the water phase and was washed for 3 times with 100 wt. parts of hot water. The 1-heptanol layer was concentrated under a reduced pressure to distill off about 80% of 1-heptanol added. The bottom residue was cooled to room temperature and filtered and washed with 100 wt. parts of toluene and dried to obtain 23.8 wt. parts of crystals. The yield was 95% based on the 4,4'-dihydroxybiphenyl formed by the hydrolysis.

The solvent solution obtained by the extraction from the alkaline aqueous solution was concentrated and neutralized to obtain crystals of p-phenylphenol. The quality is shown in Table 1.

EXAMPLES 2,3,4,5,6,7,8,9 and 10

In accordance with the process of Example 1 except varying the specific solvent, each process was carried out. The result is shown in Table 1.

EXAMPLE 11

In accordance with the process of Example 1 except varying the specific solvent, the process was repeated to the step extracting the reaction product. In the resulting solvent solution of the reaction product, 1.4 wt. parts of zinc powder and 22.3 wt. parts of conc. hydrochloric acid were added and the reduction was carried out at 85° C. for 1 hour. The treated solvent solution was further treated as the process of Example 1 to obtain white crystals of 4,4'-dihydroxybiphenyl which had less coloring than that of the product of Example 1. The result is shown in Table 1.

EXAMPLE 12

In accordance with the process of Example 11 except varying the specific solvent, and admixing 1.4 wt. parts of activated carbon powder at 85° C. for 1 hour with stirring after washing the solvent solution of the reaction product with a hot water, and filtering it in hot condition, the process repeated to obtain white crystals of 4,4'-dihydroxybiphenyl which had less coloring than that of Example 11. The result is shown in Table 1.
Reference 1:

The alkaline aqueous solution of hydrolyzed product of Example 1 was neutralized with hydrochloric acid. The precipitated reaction product in free form was filtered and washed for 7 times with water (5 times of volume of the filtered cake) and dried to obtain 27.5 wt. parts of a crude 4,4'-dihydroxybiphenyl. The result is shown in Table 1.

Reference 2:

In accordance with the process of Example 1 except eliminating the extraction from the alkaline aqueous solution of the hydrolyzed product, the process was repeated. The result is shown in Table 1. Since the extraction from the alkaline aqueous solution was eliminated, the yield of 4,4'-dihydroxybiphenyl was smaller.

The 4,4'-dihydroxybiphenyl obtained by the processes of References had lower purity.

EXAMPLE 13

In a 0.3 liter autoclave, 52.37 wt. parts of a crude 4,4'-dibromobiphenyl containing 1.19 wt. parts of 2-bromobiphenyl, 0.79 wt. part of 4-bromobiphenyl and 2.65 wt. parts of 2,4'-dibromobiphenyl and 226.8 wt. parts of 20% NaOH aqueous solution and 0.46 wt. part of cuprous oxide were charged. The autoclave was closed and purged with nitrogen and was heated. The reaction was carried out at 200° C. for 22 hours. The reaction mixture was filtered at 70°-75° C. to separate the catalyst of the cuprous oxide. The catalyst layer was washed with water. The washing water was mixed with the filtrate. The alkaline aqueous solution was heated at 80°-85° C. and was extracted for 2 times with 100 wt. parts of cyclohexanol. Then, 284 wt. parts of new cyclohexanol was added to the alkaline aqueous solution. The mixture was stirred at 80°-85° C. and neutralized with conc. hydrochloric acid. The reaction product in free form was immediately extracted into the cyclohexanol. The cyclohexanol layer was separated from the water layer and was reduced by adding 1.7 wt. parts of zinc powder and 13.6 wt. parts of conc. hydrochloric acid at 85° C. for 1 hour.

The solvent solution was further treated as the process of Example 1 to obtain 23.8 wt. parts of crystals. The yield was 93% based on 4,4'-dihydroxybiphenyl formed by the hydrolysis. The quality of the product was substantially the same as that of Example 1.

The solvent solution obtained by extraction from the alkaline aqueous solution was concentrated and neutralized to obtain 2.65 wt. parts of crystals containing 0.86 wt. part of o-phenylphenol and 1.79 wt. parts of p-phenylphenol.

TABLE 1

| | Solvent for extraction | | Yield (part) | |
|---|---|---|---|---|
| | First extraction in alkaline sol. | Second extraction in free form | p-phenyl-phenol | 4,4'-di-hydroxy-biphenyl |
| Exp. 1 | 1-heptanol | 1-heptanol | 1.25 | 23.8 |
| Exp. 2 | 1-butanol | 1-butanol | 1.28 | 22.3 |
| Exp. 3 | 1-octanol | 1-octanol | 1.20 | 22.7 |
| Exp. 4 | 2-ethylhexanol | 2-ethylhexanol | 1.18 | 22.5 |
| Exp. 5 | 1-heptanol | isophorone: 1-heptanol (3:1) | 1.25 | 23.0 |
| Exp. 6 | cyclohexanone | cyclohexanone | 1.23 | 22.9 |
| Exp. 7 | 2-hexanone | 2-hexanone | 1.22 | 22.8 |
| Exp. 8 | 4-heptanone | 4-heptanone | 1.23 | 22.5 |
| Exp. 9 | 1-heptanol | cyclohexanone | 1.25 | 22.6 |
| Exp. 10 | 2-hexanone | 1-butanol | 1.20 | 22.7 |
| Exp. 11 | 1-hexanol | 1-hexanol | 1.23 | 22.6 |
| Exp. 12 | cyclohexanol | cyclohexanol | 1.26 | 23.8 |
| Ref. 1 | — | — | — | 27.5 |
| Ref. 2 | — | 1-heptanol | — | 23.0 |

| Quality of 4,4'-dihydroxybiphenyl | | | |
|---|---|---|---|
| p-phenyl-phenol (%) | 4,4'-dihydroxy-biphenyl (%) | m.p. (°C.) | inorganic salts(ppm) |
| Exp. 1 | 0.4 | 99.0 | 278–282 | 26 |
| Exp. 2 | 0.3 | 99.2 | 279–283 | 30 |
| Exp. 3 | 0.5 | 98.9 | 278–283 | 20 |
| Exp. 4 | 0.6 | 98.5 | 277–282 | 22 |
| Exp. 5 | 0.5 | 98.9 | 278–283 | 25 |
| Exp. 6 | 0.4 | 99.1 | 278–283 | 30 |
| Exp. 7 | 0.5 | 98.8 | 277–282 | 20 |
| Exp. 8 | 0.5 | 98.9 | 277–282 | 23 |
| Exp. 9 | 0.4 | 99.0 | 278–283 | 20 |
| Exp. 10 | 0.5 | 99.0 | 278–283 | 25 |
| Exp. 11 | 0.4 | 99.1 | 278–283 | 24 |
| Exp. 12 | 0.4 | 99.1 | 278–282 | 20 |
| Ref. 1 | 5.3 | 89.7 | 265–275 | 1000 |
| Ref. 2 | 2.0 | 96.1 | 270–278 | 30 |

What is claimed is:

1. A process for producing 4,4'-dihydroxybiphenyl having high purity, which process comprises:
   hydrolyzing a crude 4,4'-dibromobiphenyl which comprises 4-bromobiphenyl, 2-bromobiphenyl and 2,4'-dibromobiphenyl in the presence of a copper compound catalyst in an alkaline aqueous solution;
   separating said copper compound catalyst from said alkali aqueous solution by filtration;
   selectively extracting alkali metal phenylphenolates as by-products from the resulting alkaline aqueous solution with an alcohol or ketone which forms an organic phase;
   separating said organic phase from said alkaline aqueous solution;
   neutralizing or acidifying the alkaline aqueous solution with an acid;
   extracting the biphenolic reaction product from said neutralized or acidified solution with an alcohol or ketone which forms an organic phase;
   separating said organic phase; and
   crystallyzing the 4,4'-dihydroxybiphenyl reaction product from said organic phase.

2. A process according to claim 1 wherein the acid is added to a mixture of the alkaline aqueous solution of the reaction product with the specific alcohol or ketone so as to extract the reaction product in free form during the addition of the acid.

3. A process according to claim 1 wherein the specific alcohol or ketone is selected from the group consisting of butanols, pentanols, hexanols, heptanols, octanols, ethylhexanols, cyclohexanols, hexanones, methylbutyl ketones, heptanones, dibutyl ketones, phorones, cyclohexanones, acetophenones and methyl cyclohexanones.

4. A process according to claim 1 wherein the extraction of by-products from the alkaline aqueous solution of the reaction product is performed at the temperature from 30° to 95° C. especially from 50° to 85° C.

5. A process according to claim 1 wherein the extraction of the reaction product in free form after the neutralization is performed at the temperature from 30° to 90° C. especially 70° to 85° C.

6. A process according to claims 1,2,3,4, or 5 wherein the solution of the reaction product is concentrated before the crystallization.

7. A process according to claim 1, wherein the solvent solution of the reaction product is treated with an activated carbon before the crystallization.

8. A process according to claim 1, wherein 2,4'-dihydroxybiphenyl is separated from 4,4'-dihydroxybiphenyl in said crystallization step of 4,4'-dihydroxybiphenyl.

9. A process according to claim 1 wherein the substantially same specific alcohol or ketone is used in both extraction steps.

* * * * *